US006250469B1

(12) United States Patent
Kline

(10) Patent No.: US 6,250,469 B1
(45) Date of Patent: *Jun. 26, 2001

(54) FORMULATIONS FOR PROTECTION OF PEG-INTERFERON ALPHA CONJUGATES

(75) Inventor: Douglas Kline, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/703,581

(22) Filed: Nov. 1, 2000

Related U.S. Application Data

(63) Continuation of application No. 09/268,423, filed on Mar. 12, 1999, now Pat. No. 6,180,096.
(60) Provisional application No. 60/079,471, filed on Mar. 26, 1998.

(51) Int. Cl.[7] .......................... B65D 69/00; B65D 71/00; A61K 38/19; A61K 38/21
(52) U.S. Cl. ..................... 206/571; 424/85.1; 424/85.4; 424/85.7; 424/46; 514/12; 530/350; 530/351; 530/388.23; 530/403; 530/405; 530/409; 530/416; 206/570; 206/569
(58) Field of Search ..................... 206/569, 570, 206/571; 530/350, 351, 388.23, 403, 405, 409, 416; 514/12; 424/85.7, 46, 85.1, 85.4

(56) References Cited

U.S. PATENT DOCUMENTS

| | | | |
|---|---|---|---|
| 5,122,614 | 6/1992 | Zalipsky | 548/520 |
| 5,595,732 | 1/1997 | Hakini et al. | 424/85.7 |
| 5,691,298 | 11/1997 | Gosselink et al. | 510/475 |
| 5,711,944 | 1/1998 | Gilbert et al. | 424/85.7 |
| 5,762,923 | 6/1998 | Gross et al. | 424/85.7 |
| 5,935,566 | 8/1999 | Yuen et al. | 424/85.7 |

FOREIGN PATENT DOCUMENTS 0 736 303 B1    8/1999   (EP) .............................. A61K/38/21

OTHER PUBLICATIONS

Lam et al., "The Effect of Benzyl Alcohol on Recombinant Human Interferon–γ" *Pharmaceutical Research*, 14:725 (1997).

The Merck Index, Merck Research Laboratories, pp. 1517–1518 (1996).

*Primary Examiner*—F. T. Moezie
(74) *Attorney, Agent, or Firm*—Donald W. Wyatt

(57) ABSTRACT

The present invention provides formulations that prevent loss and damage of PEG-interferon alpha conjugates during and following lyophilization. The formulations of the present invention protect PEG-interferon alpha conjugates from loss and degradation during the lyophilization process, as well as degradation during subsequent storage. The formulations of the present invention are suitable for protection of PEG-interferon alpha conjugates from various types of degradation, including, but not limited to loss of biological activity and changes in the degree and/or nature of conjugation. A preferred PEG-interferon alpha conjugate protectable in the formulations of the present invention is an interferon alpha-2b-polyethylene glycol (12,000) conjugate.

25 Claims, No Drawings

FORMULATIONS FOR PROTECTION OF PEG-INTERFERON ALPHA CONJUGATES

This application is a continuation of U.S. patent application Ser. No. 09/268,423 filed Mar. 12, 1999 now U.S. Pat. No. 6,180,096 which claims the benefit of U.S. provisional application Ser. No. 60/079,471 filed Mar. 26, 1998, herein incorporated by reference.

Throughout this disclosure, various publications, patents and patent applications are referenced. The disclosures of these publications, patents and patent applications are herein incorporated by reference.

FIELD OF THE INVENTION

The present invention pertains to formulations for the stabilization of PEG-interferon alpha conjugates during and after lyophilization, their production and use.

BACKGROUND OF THE INVENTION

Various natural and recombinant proteins have pharmaceutical utility. Once they have been purified, separated, and formulated, they can be parenterally administered for various therapeutic indications. However, parenterally administered proteins may be immunogenic, may be relatively water insoluble, and may have a short pharmacological half life. Consequently, it can be difficult to achieve therapeutically useful blood levels of the proteins in patients.

These problems can be overcome by conjugating the proteins to polymers, such as polyethylene glycol. Davis et al., U.S. Pat. No. 4,179,337 disclose conjugating polyethylene glycol (PEG) to proteins such as enzymes and insulin to obtain conjugates having less immunogenic effect than the original proteins and yet still retaining a substantial proportion of their physiological activity. Veronese et al., (Applied Biochem. and Biotech, 11: 141–152, 1985) disclose activating polyethylene glycols with phenyl chloroformates to modify a ribonuclease and a superoxide dimutase. Katre et cil. U.S. Pat. Nos. 4,766,106 and 4,917,888 also disclose solubilizing proteins by polymer conjugation. Likewise, PEG and other polymers can be conjugated to recombinant proteins to reduce immunogenicity and increase half-life. See Nitecki, et al., U.S. Pat. No. 4,902,502, Enzon, Inc., International Application No. PCT/US90/02133, Nishimura et al., European Patent Application 154,316 and Tomasi, International Application Number PCT/US85/02572. For example, interferon alpha-2b is known to be effective for treatment of disease states such as renal cell carcinoma, AIDS-related Kaposi's sarcoma, chronic and acute hepatitis B, chronic and acute non-A, non-B/C hepatitis and hepatitis C. Improvement of the pharmacological half-life of interferon alpha-2b would improve treatment of these conditions.

While preparation of protein-polymer conjugates is beneficial, they cannot be used in a practical manner unless they can be stored for an extended period of time during manufacture and distribution to health care providers. Some protein-polymer conjugates, however, rapidly deteriorate, even in frozen solutions. Lyophilization (also known as freeze-drying) is a process that can render a pharmaceutical in a form that can overcome this deficiency.

Lyophilization is a process whereby water is sublimed from a composition after it is frozen. In this process, pharmaceuticals and biologicals that are relatively unstable in an aqueous solution over a period of time can be placed into dosage containers in an easily processed liquid state, dried without the use of damaging heat and stored in a dried state for extended periods.

Due to the low total mass of active substance in each dose, the formulations of most pharmaceuticals and biologicals, including protein-polymer conjugates, require additional ingredients to protect the active ingredient during the lyophilization process. For example, a pharmaceutical filled into a dosage container as a low-concentration aqueous solution can be susceptible to physical loss during the lyophilization vacuum process or adsorption to the container. A lyophilized formulation often contains bulking ingredients that increase the amount of solid material, as well as cryoprotectants, lyoprotectants and other stabilizers to protect the active component from damage. Which particular formulation will protect a given type of pharmaceutical, however, must be determined empirically.

There is a present need for a formulation suitable to protect protein-polymcr conjugates, and in particular PEG-interferon alpha conjugates, from damage during lyophilization. Such a formulation should allow PEG-interferon alpha-polymer conjugates to maintain their biological activity, physical stability and chemical stability over extended periods of time.

SUMMARY OF THE INVENTION

The present invention provides formulations that permit stabilization of PEG-interferon alpha conjugates during and after lyophilization.

In one embodiment, the present invention provides aqueous formulations comprising PEG-interferon conjugates, a buffer, a stabilizer and a cryoprotectant. The present invention also contemplates processes for preparing stable, aqueous formulation solutions comprising admixing an effective amount of PEG-interferon alpha conjugates with a buffer, a stabilizer, a cryoprotectant and a solvent. In a preferred aspect of the process of the present invention, the formulation is prepared and maintained substantially free of dissolved oxygen and a head space of inert atmosphere above the formulation is maintained at a value of less than about 4% oxygen by volume.

The present invention is not limited to specific chemicals for the solution components. However, in a preferred embodiment, the buffer is sodium phosphate, the stabilizer is a poly(oxy-1,2-ethanediyl) derivative, the cryoprotectant is sucrose and the solvent is water. In such an embodiment, the sodium phosphate can comprise sodium phosphate dibasic anhydrous with sodium phosphate monobasic dihydrate.

The present invention is also not limited by the concentrations of the components of the formulations of the present invention. In one embodiment, the concentration of PEG-interferon alpha conjugates is preferably 0.03 to 2.0 mg interferon alpha per ml, while the concentration of sodium phosphate is preferably 0.005 to 0.1 molar, the concentration of poly(oxy-1,2-ethanediyl) derivative is preferably 0.01 to 1.0 mg/ml and the concentration of sucrose is preferably 20 to 100 mg/ml. In a particularly preferred embodiment, the mass of PEG-interferon conjugates is 0.1 mg of interferon alpha, the mass of sodium phosphate dibasic is 0.75 mg, the mass of sodium phosphate monobasic dihydrate is 0.75 mg, the mass of sucrose is 40 mg, the mass of poly(oxy-1,2-ethanediyl) derivative is 0.05 mg and the volume of water is 0.5 ml. Alternatively, the ratio of components is 0.08% of said PEG-interferon alpha conjugates as measured by the mass of the interferon alpha, 3.6% of sodium phosphate, 0.12% of poly(oxy-1,2-ethanediyl) derivative and 96.2% of sucrose, by weight While the present invention is not limited to a specific PEG-interferon alpha conjugate, in one embodiment, the PEG-interferon alpha conjugates comprise single PEG molecules conjugated to single interferon molecules. In such an embodiment, the interferon alpha molecules can be selected from the group consisting of interferon alpha-2a, interferon alpha-2b, interferon alpha-2c and consensus interferon. In a preferred embodiment, the interferon molecules are interferon alpha-2b. Likewise, while the present invention is not limited to a specific PEG molecule, in one embodiment, the polyethylene glycol is $PEG_{,2000}$ In a particularly preferred embodiment, the interferon alpha-2b molecules are linked to the $PEG_{12000}$ molecules with a urethane bond.

While not limited to a specific characterization, when single interferon alpha molecules are linked to single polymer molecules, the present invention contemplates that the resulting PEG-interferon alpha conjugates can comprise a mixture of positional isomers. In a preferred embodiment, one of the positional isomers is an interferon alpha-2b molecule linked to a $PEG_{12000}$ molecule at a histidine residue on the interferon alpha-2b molecule.

The present invention also contemplates a process of lyophilization, comprising lyophilization of the formulations described above to create a lyophilized powder. In a preferred embodiment, the process further comprises reconstitution of the lyophilized powder with water or other aqueous diluents, such as benzyl alcohol-containing bacteriostatic water for injection, to create a reconstituted solution (Bacteriostatic Water for Injection, Abbott Laboratories, Abbott Park, Ill.).

The present invention also contemplates lyophilized powders produced by lyophilization of the formulations described above. In a preferred embodiment, the lyophilized powder comprises 0.08% of said PEG-interferon alpha conjugates, 3.6% of said sodium phosphate, 0.12% of said poly(oxy-1,2-ethanediyl) derivative and 96.2% of said sucrose, by weight.

Likewise, articles of manufacture comprising a syringe or a vial containing an effective amount of such lyophilized powders is contemplated. In a preferred embodiment, the article of manufacture further comprises a volume of water for reconstitution of the powder. In a particularly preferred embodiment, the powder is reconstituted with bacteriostatic water. In a further preferred embodiment, the lyophilized powder is reconstituted with the same volume of water as was removed from the lyophilization solution during lyophilization.

The present invention also contemplates processes for treating diseases in animals. In one embodiment, this process comprises the introduction of the reconstituted solution into an animal having a disease. In one embodiment, the animal is human. In a preferred embodiment, the human is infected with a hepatitis virus, such as hepatitis C virus. In an alternate preferred embodiment, the human has cancer.

DETAILED DESCRIPTION OF THE INVENTION

"PEG-interferon alpha conjugates" are interferon alpha molecules covalently attached to a PEG molecule. In preferred embodiments, the PEG-interferon alpha conjugates of the present invention comprises interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany) or consensus interferon as defined by determination of a consensus sequence of naturally occurring interferon alphas (Infergen, Amgen, Thousand Oaks, Calif.).

Polymers, on the other hand, are molecules having covalently attached repeating chemical units. Often, the approximate molecular weight of the polymer is designated with a number following the name of the repeated chemical unit. For example, "$PEG_{12000}$" or "polyethylene glycol (12,000)" refers to a polymer of polyethylene glycol having an average molecular weight of approximately 12,000. In a $PEG_{12000}$ polymer, the number of repeated polyethylene glycol units in the polymer is approximately 273. It is understood that these designations are approximate as polymers are manufactured in the form of a mixture having a distribution of chain lengths, giving an average molecular weight, and it is often impossible to manufacture a polymer having a precise and uniform molecular weight or number of repeated units. Various other polymers and their methods for production are well known in the art.

Methods for creating protein-polymer conjugates are also known in the art. For example, U.S. Pat. No. 5,691,154 to Callstrom et al, U.S. Pat. No. 5,686,071 to Subramanian et al, U.S. Pat. No. 5,639,633 to Callstrom et al, U.S. Pat. No. 5,492,821 to Calistrom et al, U.S. Pat. No. 5,447,722 to Lang et al and U.S. Pat. No. 5,091,176 to Braatz et al all provide methods for producing protein-polymer conjugates.

Conjugation of polymers to proteins may result in a single polymer molecule conjugated to a protein or multiple such conjugations to a single protein. The degree of conjugation is dependent upon the reaction conditions and desired result. In a preferred embodiment, the PEG-interferon alpha conjugate in the formulations of the present invention comprises a single interferon alpha-2b conjugated to a single $PEG_{12000}$. In a particularly preferred embodiment, the interferon alpha-2b molecule is linked to the $PEG_{12000}$, molecule with a urethane bond. Reagents and methods for producing this protein-polymer conjugate can be found in U.S. Pat. No. 5,612,460 to Zalipsky and U.S. Pat. No. 5,711,944 to Gilbert, et al. When such a protein-polymcr conjugate is utilized in the formulation solutions of the present invention, the preferred concentration of PEG-interferon alpha conjugate is 0.03 to 2.0 mg interferon alpha per ml.

When a single interferon alpha molecule is linked to a single polymer molecule, the resulting PEG-interferon alpha conjugates may be in the form of a single positional isomer or in a mixture of positional isomers. A "mixture of positional isomers" indicates that the individual PEG-interferon alpha conjugates may be linked at different sites on different interferon alpha molecules. For example, in one embodiment of the present invention, the PEG-interferon alpha mixture contains at least one PEG-interferon alpha conjugate linked at a histidine residue of the interferon alpha molecule, while another PEG-interferon alpha conjugate is linked at another site of the interferon alpha molecule (e.g. the amino terminus).

As described above, preservation of PEG-interferon alpha conjugates can be achieved by lyophilization. Lyophilization is a process of freeze-drying a composition wherein a frozen aqueous mixture is treated to remove water. Commonly, the process involves the sublimation of water from the frozen aqueous solutions, usually under reduced pressure conditions. After lyophilization, the PEG-interferon alpha conjugate can be stored for extended periods of time.

PEG-interferon alpha conjugates, however, are subject to damage during and after lyophilization. Damage to PEG-interferon alpha conjugates can be characterized by the loss of protein, loss of biological activity or by the change in the degree and/or nature of conjugation of the interferon alpha. For example, a PEG-interferon alpha conjugate may degrade into free PEG and interferon alpha, resulting in a lowering of the degree of conjugation. Likewise, the resulting free PEG may become available to conjugate to another interferon alpha, potentially resulting in the increase of the degree of conjugation in that target molecule. Similarly, a PEG-interferon alpha conjugate may undergo an intramolecular shift of the PEG from one site of conjugation to another within the same molecule, thereby changing the nature of conjugation of the interferon alpha.

The present invention protects PEG-interferon alpha conjugates from damage by including them in formulations that prevent damage during and after lyophilization. While the present invention is not limited to a particular formulation, in a preferred embodiment, the method utilizes a buffer, stabilizer, cryoprotectant and solvent, in addition to the PEG-interferon alpha conjugate.

Buffers are suitable for maintaining the pH of the formulation in a range of 4.5 to 7.1, preferably 6.5–7.1 and most preferably 6.8. The use of a buffer system of sodium phosphate dibasic and sodium phosphate monobasic is preferred. When a sodium phosphate dibasic anhydrous/monobasic dihydrate system is utilized, it is preferably in equal mass amounts of dibasic to monobasic at a preferred total concentration of 0.005 to 0.1 molar. Other suitable buffer systems to maintain the desired pH range include sodium citrate/citric acid and sodium acetate/acetic acid.

A stabilizing agent is useful to prevent adsorption of the PEG-interferon alpha conjugate to the stainless steel and glass surfaces of the equipment used to make and store the formulations containing the PEG-interferon alpha conjugate. As one example, poly(oxy-1,2-ethanediyl) derivatives are useful as stabilizing agents. Mono-9-octadecenoate poly (oxy- 1,2-ethanediyl) derivatives (Polysorbate 80) is a preferred stabilizing agent. When polysorbate 80 is utilized, the preferred concentration is 0.01 to 1 mg/ml.

Cryoprotectants, also known as cryoprotective agents or compounds, are agents that protect chemical compounds, cells, or tissues from the deleterious effects of freezing, such as that usually accompanying lyophilization. In the case of PEG-interferon alpha conjugates, cryoprotectants can protect them from damage, adsorption and loss from vacuum utilized in lyophilization.

While the present invention is not limited to a specific cryoprotectant, examples include, but are not limited to, carbohydrates such as the saccharides, sucrose, sugar alcohols such as mannitol, surface active agents such as the Tweens, as well as glycerol and dimethylsulfoxide. A preferred cryoprotectant is a carbohydrate. A preferred carbohydrate is a saccharide or disaccharide. A preferred disaccharide is sucrose.

Likewise, the present invention is not limited to any particular amount of cryoprotectant used. In one embodiment, cryoprotectants are present in an amount sufficient to allow the PEG-interferon alpha conjugate to be lyophilized. In such an embodiment, cryoprotectants can be present in an amount of 0.05% to 90%, preferably 0.05–50%, and most preferably in an amount of about 0.15% to about 10%, based on the total weight of the PEG-interferon alpha solution. When sucrose is used, the preferred concentration is 20 to 100 mg/ml.

Formulations including an effective amount of biologically active PEG-interferon alpha conjugates arc useful in treating disease states, preferably as injectable aqueous solutions. An effective amount means the formulation or powder has an adequate concentration of biologically active component to treat a disease state in an animal. For example, the preferred interferon alpha-2b-$PEG_{12000}$ conjugates are suitable for treatment of disease states such as renal cell carcinoma, AIDS-related Kaposi's sarcoma, chronic and acute hepatitis B, chronic and acute non-A, non-B/C hepatitis and hepatitis C. One solution containing an effective amount of this PEG-interferon alpha conjugate contains 0.03 to 2.0 mg/ml of $PEG_{12000}$-interferon alpha-2b conjugate as measured by protein mass.

EXAMPLE

This example provides a description of a formulation of the present invention and protection of one PEG-interferon alpha conjugate during lyophilization and storage. The PEG-interferon alpha conjugate is introduced in a lyophilization formulation, lyophilized and stored as a dry powder. The components of the formulation are as follows:

TABLE 1

Formulation for Lyophilization and Storage

| Component | mg/vial* |
|---|---|
| interferon alfa-2b-$PEG_{12000}$ | 0.1*** |
| Sodium Phosphate Dibasic Anhydrous | 0.75 |
| Sodium Phosphate Monobasic Dihydrate | 0.75 |
| Sucrose | 40 |
| Polysorbate 80 | 0.05 |
| Water for Injection (q.s. ad) | 0.5 ml** |

*Amount contained in label volume of 0.5 ml
**Water is sublimed during lyophilization.
***Based on protein mass.

After lyophilization, the resulting powder is stored and, over a period of six months, samples are reconstituted with water for analysis. The reconstituted solution is analyzed for protein mass content, degree of conjugation of the PEG-interferon alpha conjugate, bioactivity and visual clarity. The results are present in Table 2.

TABLE 2

Stability Data
Stability Data on 100 μg vial

| Time months | Temp. °C. | Antiviral Assay | | Protein Content | | Purity of PEG-IFN | | | | |
|---|---|---|---|---|---|---|---|---|---|---|
| | | ×10$^6$ IU/vial* | % LS | μg/vial* | % of Initial | % di-PEG-IFN | % mono PEG-IFN | % IFN | % Other | Descr. |
| Initial | | 4.33 | 76 | 95.8 | 95.8 | 3.90 | 94.19 | 1.91 | | CCS** |
| 1 | 5 | 6.60 | 115 | 95.6 | 95.6 | 3.70 | 94.20 | 2.10 | 0 | CCS |
| | 25 | 7.50 | 131 | 96.4 | 96.4 | 3.84 | 93.76 | 2.40 | 0 | CCS |
| | 40 | 7.30 | 128 | 96.2 | 96.2 | 3.52 | 92.11 | 4.37 | 0 | CCS |
| 3 | 5 | 6.60 | 116 | 97.1 | 97.1 | 3.48 | 94.27 | 2.25 | 0 | CCS |
| | 25 | 6.55 | 115 | 98.0 | 98.0 | 3.47 | 93.82 | 2.72 | 0 | CCS |

TABLE 2-continued

Stability Data
Stability Data on 100 μg vial

| Time months | Temp. °C. | Antiviral Assay ×10⁶ IU/vial* | % LS | Protein Content μg/vial* | % of Initial | Purity of PEG-IFN % di-PEG-IFN | % mono PEG-IFN | % IFN | % Other | Descr. |
|---|---|---|---|---|---|---|---|---|---|---|
| 6 | 5 | 6.20 | 109 | 92.6 | 92.6 | 3.95 | 93.60 | 2.45 | 0 | CCS |
|   | 25 | 6.25 | 110 | 93.3 | 93.3 | 3.76 | 92.96 | 3.28 | 0 | CCS |
| 9 | 5 | 6.85 | 120 | 94.1 | 94.1 | 3.59 | 94.02 | 2.39 | 0 | CCS |
|   | 25 | 5.75 | 101 | 96.1 | 96.1 | 3.69 | 92.91 | 3.40 | 0 | CCS |

*Label fill is 0.5 ml/vial
**CCS: White powder; after reconstitution, a clear, colorless solution, essentially free from visible particles The results show that the total protein mass content is relatively stable over the nine-month period. Additionally, the change in degree of the monopegylated interferon alfa-2b (i.e., degradation to free interferon and polymer or creation of dipegylated interferon) negligible. The bioactivity as measured by a cell-based antiviral assay remains essentially unchanged. The reconstituted solutions remain clear, colorless and free from visible particles throughout the six-month period. This demonstrates a surprisingly high stability during lyophilization and subsequent storage.

From the above, it is clear that the present invention provides formulations suitable to protect PEG-interferon alpha conjugates from damage during lyophilization and during subsequent storage.

I claim:

1. An article of manufacture, comprising a container containing a lyophilized powder produced by lyophilizing a solution comprising PEG-interferon alpha conjugates, a buffer, a stabilizer, a cryoprotectant and a solvent, wherein said buffer is sodium phosphate, said stabilizer is a poly (oxy-1,2-ethanediyl), said cryoprotectant is sucrose and said solvent is water.

2. The article of claim 1, wherein said container is a syringe.

3. The article of claim 2, wherein said sodium phosphate comprises sodium phosphate dibasic anhydrous and sodium phosphate monobasic dihydrate.

4. The article of claim 3, wherein the mass of said PEG-interferon alpha conjugates is 0.1 mg of interferon alpha, the mass of said sodium phosphate dibasic anhydrous is 0.75 mg, the mass of said sodium phosphate monobasic dihydrate is 0.75 mg, the mass of said sucrose is 40 mg, the mass of said poly(oxy- 1,2-ethanediyl) is 0.05 mg and the volume of said water is 0.5 ml.

5. The article of claim 2, wherein said PEG-interferon alpha conjugates comprise single PEG molecules conjugated to single interferon alpha molecules.

6. The article of claim 5, wherein said interferon alpha molecules are selected from the group consisting of interferon alpha-2a, interferon alpha-2b, interferon alpha-2c and consensus interferon.

7. The article of claim 6, wherein said polyethylene glycol is $PEG_{12000}$.

8. The article of claim 7, wherein said interferon alpha molecules are interferon alpha-2b.

9. The article of claim 8, wherein said interferon alpha-2b molecules are linked to said $PEG_{12000}$ molecules with a urethane bond.

10. The article of claim 9, wherein said PEG-interferon alpha conjugates comprise a mixture of positional isomers.

11. The article of claim 10, wherein one of said positional isomers comprises said interferon alpha-2b molecule linked to said $PEG_{12,000}$ molecule at a histidine residue on said interferon alpha-2b molecule.

12. The article of claim 2, further comprising a volume of water for reconstitution of said powder.

13. The article of claim 12, wherein said water comprises bacteriostatic water.

14. The article of claim 1, wherein said container is a vial.

15. The article of claim 14, wherein said sodium phosphate comprises sodium phosphate dibasic anhydrous and sodium phosphate monobasic dihydrate.

16. The article of claim 15, wherein the mass of said PEG-interferon alpha conjugates is 0.1 mg of interferon alpha, the mass of said sodium phosphate dibasic anhydrous is 0.75 mg, the mass of said sodium phosphate monobasic dihydrate is 0.75 mg, the mass of said sucrose is 40 mg, the mass of said poly(oxy-1,2-ethanediyl) is 0.05 mg and the volume of said water is 0.5 ml.

17. The article of claim 14, wherein said PEG-interferon alpha conjugates comprise single PEG molecules conjugated to single interferon alpha molecules.

18. The article of claim 17, wherein said interferon alpha molecules are selected from the group consisting of interferon alpha-2a, interferon alpha-2b, interferon alpha-2c and consensus interferon.

19. The article of claim 18, wherein said polyethylene glycol is $PEG_{12000}$.

20. The article of claim 19, wherein said interferon alpha molecules are interferon alpha-2b.

21. The article of claim 20, wherein said interferon alpha-2b molecules are linked to said $PEG_{12000}$ molecules with a urethane bond.

22. The article of claim 21, wherein said PEG-interferon alpha conjugates comprise a mixture of positional isomers.

23. The article of claim 22, wherein one of said positional isomers comprises said interferon alpha-2b molecule linked to said $PEG_{12000}$ molecule at a histidine residue on said interferon alpha-2b molecule.

24. The article of claim 14, further comprising a volume of water for reconstitution of said powder.

25. The article of claim 24, wherein said water comprises bacteriostatic water.

* * * * *